(12) United States Patent
Olivo et al.

(10) Patent No.: US 7,585,667 B2
(45) Date of Patent: *Sep. 8, 2009

(54) NEGATIVE STRAND RNA VIRUS REPLICON

(75) Inventors: Paul D. Olivo, St. Louis, MO (US); Peter L. Collins, Kensington, MD (US); Mark E. Peeples, Bexley, OH (US)

(73) Assignees: The United States of America as represented by The Department of Health and Human Services, Washington, DC (US); Rush University Medical Center, Chicago, IL (US)

( * ) Notice: Subject to any disclaimer, the term of this patent is extended or adjusted under 35 U.S.C. 154(b) by 25 days.

This patent is subject to a terminal disclaimer.

(21) Appl. No.: 10/560,655

(22) PCT Filed: Jun. 14, 2004

(86) PCT No.: PCT/US2004/018783

§ 371 (c)(1), (2), (4) Date: Aug. 11, 2006

(87) PCT Pub. No.: WO2005/005645

PCT Pub. Date: Jan. 20, 2005

(65) Prior Publication Data

US 2006/0275774 A1 Dec. 7, 2006

Related U.S. Application Data

(60) Provisional application No. 60/478,521, filed on Jun. 13, 2003.

(51) Int. Cl.
- *C12N 15/86* (2006.01)
- *C12N 7/01* (2006.01)
- *C12N 15/45* (2006.01)

(52) U.S. Cl. .................. 435/320.1; 435/235.1; 435/325; 536/23.72

(58) Field of Classification Search ....................... None
See application file for complete search history.

(56) References Cited

U.S. PATENT DOCUMENTS 6,270,958 B1 * 8/2001 Olivo et al. .................... 435/5
7,226,786 B2 * 6/2007 Kitazato et al. ............. 435/456

FOREIGN PATENT DOCUMENTS

WO  WO 00/70070  * 11/2000

(Continued)

OTHER PUBLICATIONS

Whelan et al. Transcription and replication of nonsegmented negative-strand RNA viruses. Curr Top Microbiol. Immunol. 2004; 283:61-119.*

(Continued)

*Primary Examiner*—Mary E Mosher
*Assistant Examiner*—Stuart W Snyder
(74) *Attorney, Agent, or Firm*—Thompson Coburn LLP; Charles P. Romano (57) ABSTRACT

The present invention relates to non-cytopathic negative-strand RNA virus replicons, and methods of making and using the replicons and replicon systems.

18 Claims, 6 Drawing Sheets

FOREIGN PATENT DOCUMENTS

| | | |
|---|---|---|
| WO | WO 01/19853 A2 | 3/2001 |
| WO | WO 03/025570 A | 3/2003 |
| WO | WO 03/025570 A1 | 3/2003 |
| WO | WO 03/029274 A | 4/2003 |
| WO | WO 2005/005645 A1 | 1/2005 |

OTHER PUBLICATIONS

Nagai and Kato, Paramyxovirus Reverse Genetics Is Coming of Age. Microbiol. Immunol. 1999, 42(7); 613-624.*

Heminway, et al. Analysis of Respiratory Syncytial Virus F, G, and SH Proteins in Cell Fusion. Virology. 1994; 200(2):801-805. Abstract Only.*

Kimura, et al. Cloning of the blasticidin S deaminase gene (BSD) from *Aspergillus terreus* and its use as a selectable marker for *Schizosaccharomyces pombe* and *Pyricularia oryzae*.Mol Gen Genet. Jan. 1994;242(2):121-9. Abstract Only.*

Oomens, A. G. P. et al; Infectivity of a Human Respiratory Syncytial Virus Lacking the SH, G, and F Proteins is Efficiently Mediated by the Vesicular Stomatitis Virus G Protein; Journal of Virology, Mar. 2003, pp. 3785-3798, vol. 77, No. 6; American Society of Microbiology.

Techaarpornkul, Sunee et al; Functional Analysis of Recombinant Respiratory Syncytial Virus Deletion Mutants Lacking the Small Hydrophobic and/or Attachment Glycoprotein Gene; Journal of Virology, Aug. 2001, pp. 6825-6834, vol. 75, No. 15, American Society for Microbiology.

International Search PCT/US2004/18783, Feb. 22, 2005, Olivo, Paul David.

* cited by examiner

NEGATIVE STRAND RNA VIRUS REPLICON

This application is a U.S. National Phase application of PCT/UA2004/018783, filed Jun. 14, 2004, which claims the benefit of U.S. Provisional Application No. 60/478,521, filed Jun. 13, 2003.

A Computer Readable Form of the Sequence Listing (on file "50664 Seq Listing_$_{ST}$25.txt", created on Jan. 7, 2009 and which is 727 bytes as measured in MS-WINDOWS operating system) is incorporated herein by reference.

BACKGROUND

Respiratory syncytial virus (RSV) is an important human respiratory pathogen, particularly for infants and older adults (Falsey and Walsh, 2000; Heilman, 1990). It is a single strand, non-segmented, negative sense RNA virus in the *Mononegavirales* superfamily, the *Paramyxoviridae* family, and the *Pneumovirinae* subfamily. All of the paramyxoviruses enter target cells by fusion at neutral pH, mediated by a similar fusion (F) protein and replicate entirely in the cytoplasm. The F protein expression in infected cells is also responsible for the typical syncytial pathology caused by RSV, the generation of multinucleated giant cells. RSV differs from viruses in the other *Paramyxoviridae* subfamily, the *Paramyxovirinae*, in several ways: its genome contains 10 genes, instead of 6 or 7; it has two nonstructural protein genes (NS1 and NS2) that precede the nucleocapsid (N) gene; and its attachment-enhancing protein, G (glycoprotein), is highly decorated with O-linked carbohydrate chains (Collins, Mcintosh, and Chanock, 2001).

The 15.2 kb RSV genome replicates and expresses its genes in the cytoplasm of host cells. It is encased in a helical nucleocapsid structure provided by the N protein. This nucleocapsid complex is used by the viral polymerase as the template for transcription of mRNA and for production of full-length antigenomic copies. These antigenomes are also encased in helical nucleocapsid structures by the N protein and are copied by the polymerase to produce genomes.

The major polymerase subunit is the L (large) protein, but the P (phosphoprotein) is also required for polymerase activity. While the L and P proteins are adequate for genome and antigenome synthesis, a third component, the M2-1 protein, is required for transcription of mRNA. It prevents premature termination during transcription of long mRNAs (Collins et al., 1996). Transcription of each gene initiates at a conserved 10 nt gene start (GS) sequence and terminates at a relatively conserved gene end (GE) sequence (Collins, McIntosh, and Chanock, 2001). M2-2, a second protein encoded by the M2 mRNA controls the balance between transcription and replication (Bermingham and Collins, 1999).

The viral F, G and SH (small hydrophobic) glycoproteins are synthesized in the endoplasmic reticulum and transit through the Golgi where the F protein is cleaved in two places by a furin-like enzyme (Zimmer, Budz, and Herrier, 2001) to reach the cell surface. Once at the cell surface, the F protein can cause the membranes of infected immortalized cells in culture to fuse with those of neighboring cells, producing multinucleated giant cells called syncytia. Syncytia formation does not require the G protein, but is enhanced by its presence (Karron et al., 1997; Techaarpornkul, Barretto, and Peeples, 2001). Syncytia formation is also thought to be the main cytopathic effect caused by RSV, and the main reason that RSV-infected cells die. RSV infection of cultured immortal cells does not lead to an early shutdown of protein synthesis (Levine, Peeples, and Hamilton, 1977) as do other, highly cytotoxic negative strand viruses.

Interestingly, RSV inoculation of cultured well-differentiated human airway epithelial (WD-HAE) cells results in infection of only the ciliated cells at the superficial surface but infection does not result in syncytia or in rapid cell death (Zhang et al., 2002). More recent experiments have demonstrated that these infected cells are killed by RSV infection, but that this process takes 5 to 7 days (Zhang, L, Peeples, M. E., Collins, P. L., and Pickles, R., unpublished data), indicating that RSV infection is slowly toxic for these cells even in the absence of syncytia formation.

Virion assembly takes place at the plasma membrane, orchestrated by the matrix (M) protein and culminating in the budding and release of progeny virions. In addition to their roles in virion infectivity, the G protein has been shown to enhance release of virions from infected cells (Techaarpornkul, Barretto, and Peeples, 2001). In other paramyxoviruses, and the F protein has also been shown to be important for budding (Cathomen, Naim, and Cattaneo, 1998; Russell, Jardetzky, and Lamb, 2001; Schmitt et al., 2002; Waning et al., 2002). However, RSV, like other negative strand RNA viruses, should not require its glycoproteins for genome replication and gene expression.

Non-cytotoxic replicons have previously been generated for positive strand RNA viruses, such as Sindbis and hepatitis C virus, by removing the viral glycoprotein and capsid genes (Blight, Kolykhalov, and Rice, 2000; Frolov et al., 1999; Lohmann, 1999). Replication proteins did not need to be supplied separately for these positive strand viruses because the positive strand genome is also an mRNA and is translated to produce these proteins.

DESCRIPTION OF THE FIGURES

D46 is the original full-length RSV cDNA used to rescue recombinant, infectious RSV (Collins et al., 1995). The MP224 cDNA has the enhanced GFP gene inserted in the first position, upstream of the first natural gene, NS1 (Hallak, 2000). The SN3 cDNA was derived from MP224 by deleting the three viral glycoprotein genes (Techaarpornkul, Barretto, and Peeples, 2001), replacing them with two unique restriction sites, PvuI and XhoI. YM6 was derived from SN3 by inserting a BsiWI restrictin site after the L gene and before the trailer sequence. A modified bsd gene unit from MP282 was cloned into the PvuI/XhoI sites in YM6 to generate MP295. The thick vertical bar at the left end of each cDNA represents the leader sequence, and the bar at the right end represents the trailer sequence.

Seven plasmids were transfected into HeLa cells, which were also infected with MVA-T7, a recombinant vaccinia virus mutant that contains the gene for T7 polymerase. T7 polymerase initiates RNA transcription at the T7 promoter (black box). The N, P, M2-1 and L mRNAs encode these proteins, which enable the antigenomic RNA produced from the SN3 or YM6 plasmid to replicate. The mRNAs from the F and G plasmids are translated into the F and G glycoproteins. Replicon/virions are produced and released into the medium which is used to inoculate fresh HeLa cells. GFP production identifies cells containing replicons.

The bsd gene was inserted into YM6 to generate the replicon cDNA, MP295. The sequence flanking the bsd gene is indicated in this diagram. The upstream flanking sequence comprising IG-M/SH and PvuI sequences is SEQ ID:1. The downstream flanking sequence comprising XhoI and IG-F/M2 sequences is SEQ ID NO:2. To produce replicon RNA during the launch process (FIGS. 1 and 4), the T7 polymerase initiates transcription at the T7 promoter and produces full-length antigenomic RNA, terminated at the T7 terminators. The rebozyme sequence then cleaves itself from the transcript.

Five plasmids were transfected, each containing a T7 promoter (black box) that is used by the T7 polymerase to drive transcription. The T7 polymerase was produced by the Sindbis virus SR-19-T7 replicon in these cells. The MP295 plasmid transcript represents the RSV genome with the additional GFP and bsd genes, and all three glycoprotein genes deleted. The four support plasmids shown on the left generate mRNAs that are translated into the proteins needed to launch RSV replication.

Total RNA was extracted from uncloned RSV replicon-containing BHK-SR19-T7 cells (lane 1) and the supernatant from these cells (lane 2), or from RSV-infected cells (lane 3) and their supernatant (lane 4). A reaction without the addition of RNA was included as a negative control (lane 5). The RT reaction used random hexamers for priming. Specific primer pairs for each of the viral genes listed on the left were employed for PCR. PCR products from the replicon-containing cell RNA represented the M protein gene, but not the glycoprotein genes, SH, G and F.

The replicon produces all of the RSV proteins except for its glycoproteins. To mobilize a replicon from a cell line in which it is replicating, a viral glycoprotein gene, the vesicular stomatitis virus G gene, was transfected into the replicon-containing cell line. The G glycoprotein complements the RSV replicon, allowing the formation and secretion of replicon/virions. The medium can be used to inoculate fresh cells, which in the presence of blasticidin, form colonies of replicon-containing cells.

DESCRIPTION

Described herein are materials and methods useful for developing replicons and replicon systems for negative strand RNA viruses. While the discussion and examples are directed mainly to RSV, the description should not be read as limited to that virus, as the methods are generally applicable to any negative strand RNA virus. RSV simply serves, for the purpose of this application, as a model for making and using such replicons and replicon systems.

Negative strand RNA virus replicons and replicon systems may be useful for many purposes, including as a means of testing for anti-viral agents. Such a method may comprise contacting a cell line containing a replicon with a candidate agent and then testing for an increase or decrease in replication or activity of the RNA virus replicon as compared to a control cell line harboring the same replicon, but which has not been contacted with the candidate agent.

Further, a negative strand RNA virus replicon system will be useful for researching basic questions about negative strand RNA virus biology, and also in the development of negative strand RNA viruses as viral vectors. Basic biology uses include testing the ability of mutant F and/or G genes to support virion particle formation and infectivity. These mutant genes could be transfected into the replicon cell line, and metabolically labeled virions collected to assess virion particle formation. Such a system would allow relatively facile study of the requirements for these glycoprotein genes in virion assembly, without the need for building the mutant genes into the full-length clone and rescuing virus. It would also allow avoidance of the dilemma of "un-rescueable" mutant viruses. In these cases, the inserted mutation could be lethal or another lethal mutation might have crept into the plasmid during growth in bacteria. In addition, such systems would enable direct study of severe or lethal mutations, and distinguish a problem in virion formation from a problem in protein function. These questions cannot be addressed in a clone that is unable to be rescued.

A non-cytotoxic negative strand RNA virus replicon may also be useful as a vector for long term, cytoplasmic expression of foreign genes in cultured cells. The present Sindbis virus vectors are capable of expressing large amounts of foreign proteins, but are cytotoxic. Modified Sindbis vectors that are not cytotoxic are also not capable of expressing large amounts of foreign protein. The non-cytopathic Sindbis replicon also only replicates in a limited number of cell types.

A negative strand RNA virus replicon system might also form the basis for producing negative strand RNA virus vectors, for gene therapy, for example. RSV, for example could be used to deliver genes to the respiratory tract. RSV is a good candidate for such a vector because it infects the superficial layer of the respiratory tract, unlike adenovirus which infects the basal cells (Zhang et al., 2002). For instance, an RSV replicon containing the CFTR gene that is defective in cystic fibrosis could be established in a cell line that also contains the G and F genes under the control of a Tet promoter. When doxycycline is added, virions would be produced. This "pseudovirus" could then infect cells in the respiratory tract of a CF patient and express the CFTR channel without expressing the G and F proteins. The lack of F expression not only prevents virion spread but also removes the major CTL target, so that the virus might evade immune detection and destruction.

A non-cytopathic negative strand virus replicon may be constructed as shown in the examples herein using materials and methods generally known to those of skill in the art. Such replicons may be constructed from a full length cDNA by removing, or rendering inoperative, one or more glycoprotein gene units, and inserting a gene suitable for selection. Optionally, a reporter gene may be inserted for ease of identifying replicon containing cells. For example, in the case of RSV, the F glycoproteins may be deleted or inactivated, with or without the deletion or inactivation of the SH and/or G glycoprotein genes, and a gene suitable for selection inserted.

Examples of genes suitable for selection are known in the art, including antibiotic resistance genes, that confer resistance to puromycin, hygromycin, neomycin, blastocidin and zeocin. Any reporter gene product is suitable for use, and is preferably one that can easily be assayed for. Examples include hydrolases or oxidoreductases and enzymes such as β-glucosidase, β-glucuronidase, β-galactosidase, β-hexosaminidsae, β-lactamase, luciferase, phospholipase, and phosphatase. Green fluorescent protein (GFP) is a widely used reporter gene product suitable for use, as would be other modified versions of GFP that fluoresce at a different wavelength, producing blue, yellow, cyan or red signals, or other autofluorescent proteins like the red fluorescent protein.

Figure 2:
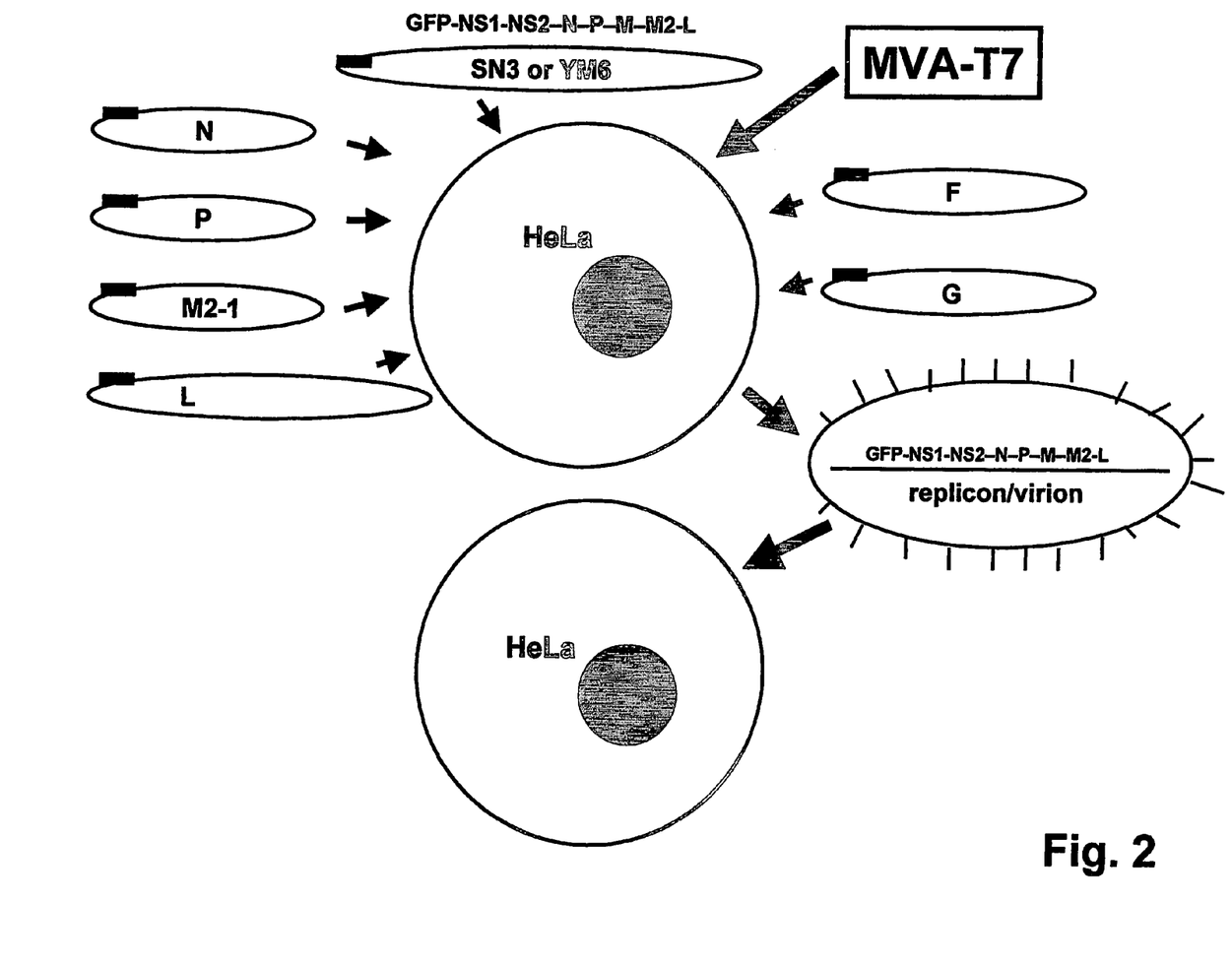
FIG. 2: Schematic representation of the launch of replicons SN3 and YM6 in HeLa cells.
Figure 6:
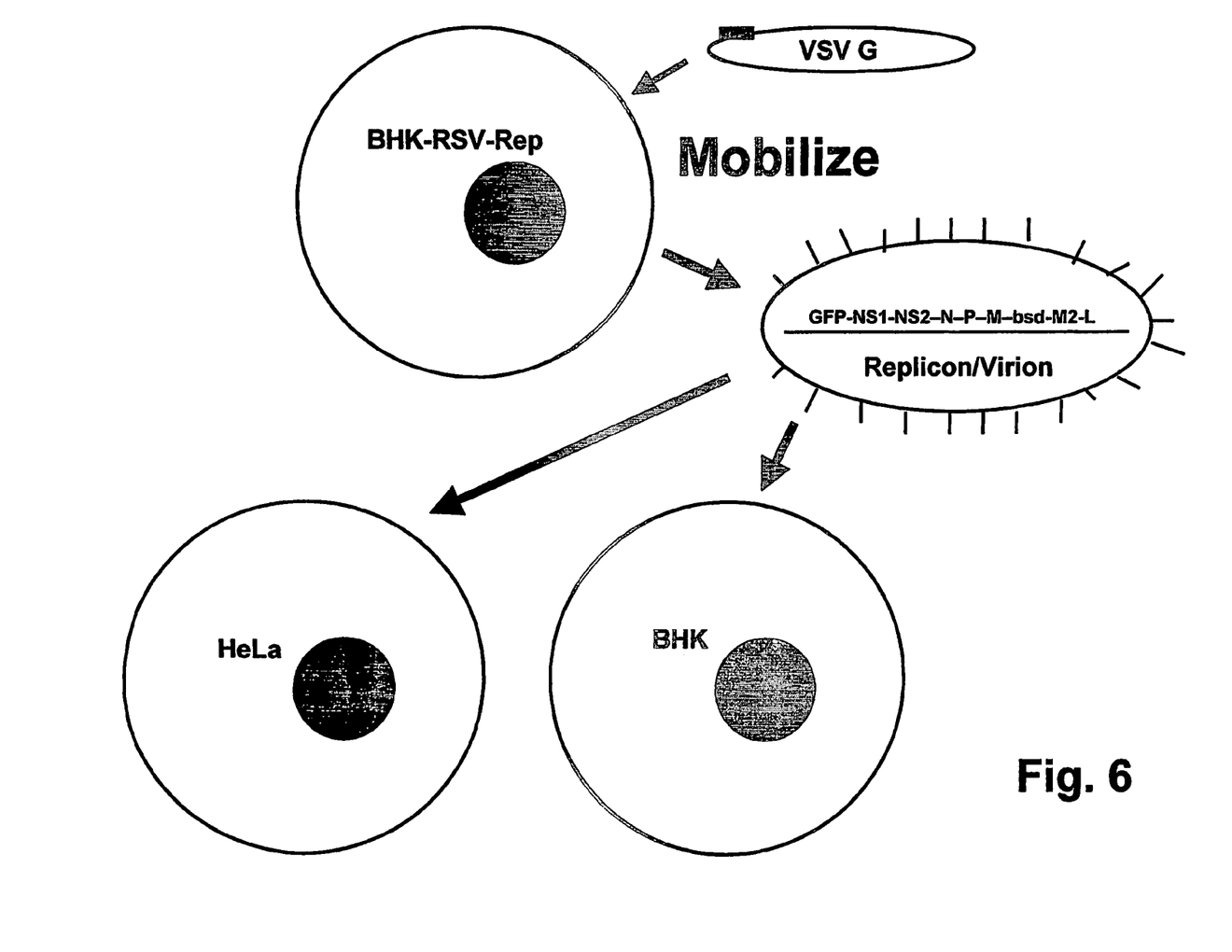
FIG. 6: Schematic representation of strategy for mobilizing a negative strand RNA virus replicon.

The strategies for "launching" a negative strand RNA virus replicon using T7 polymerase, and for "mobilizing" it into cells that do not express T7 polymerase is presented in FIGS. 2 and 6. To launch a negative strand virus replicon, a plasmid containing replicon cDNA is transfected into cells that express T7 polymerase, as illustrated in FIG. 2. In addition, support plasmids are transfected that generate the viral proteins necessary for replication and mRNA synthesis. The cells are then subjected to selection, and replicon-expressing cells are identified from the survivors. Those replicons can then be "mobilized" by transfecting their host cells with a plasmid encoding a viral glycoprotein that allows virion formation, as illustrated in FIG. 6.

Expression vectors and expression systems are well known in the art and widely available. Any suitable expression vector or system may be used, including the T7 system described in the Examples. Other examples include expression vectors containing RNA polymerase II promoters such as the cytomegalovirus (CMV) immediate early (IE) promoter and the SV40 early promoter.

As indicated above, the materials and methods disclosed herein are not narrowly limited to RSV, but rather are applicable to any negative strand RNA virus. For example, negative strand non-segmented RNA viruses, such as other members of the *Paramyxoviridae*, as well as members of the *Rhabdoviridae, Filoviridae*, and *Bornaviridae* families could be constructed from a full-length viral cDNA by removing or inactivating one or more glycoprotein gene units and inserting a gene that encodes a selectable gene product, such as an antibiotic resistance gene. A marker gene could optionally be inserted, such as GFP. Similarly, negative strand segmented RNA viruses such as *Orthomyxoviridae, Arenaviridae*, and *Bunyaviridae* could be constructed by removing one or more glycoprotein genes from the cDNA segment representing that gene and inserting a gene that encodes a selectable gene product, such as an antibiotic resistance gene. For example, in the case of viruses in the family *Orthomyxovirdae*, the virion contains 7 (influenza virus type C) or 8 (influenza virus types A and B) unique segments. In the segment containing the hemagglutinin gene, that coding sequence could be replaced with the coding sequence for an antibiotic resistance gene. Additionally, in the segment containing the neuraminidase gene, that coding sequence could be replaced with the gene encoding GFP, or another marker protein.

Rescue systems have been designed for members of most of these single strand and segmented negative strand RNA virus families that would allow the launch of a replicon. These systems are similar to the RSV system described herein. Plasmids carrying the genome or genome segments are transfected into cells, along with support plasmids, whose transcription into mRNA and the translation of the mRNAs into viral proteins provides all the protein needed to launch viral replication. Once viral replication has initiated, antibiotic treatment would kill most cells lacking a replicon, leaving clones of cells that contain viable, replicating, antibiotic resistance gene-expressing replicons. From those cells, replicons that are non-cytotoxic could be biologically selected since they would not kill their host cell. The cells containing those non-cytotoxic replicons could be cloned and used as described for RSV.

WORKING EXAMPLES

The following materials and methods are utilized in the examples:

Cells. The baby hamster kidney (BHK) cell line carrying the non-cytotoxic Sindbis virus replicon that expresses T7 polymerase, BHKSR19-T7, was a gift from Charles Rice (Rockefeller University). It was maintained in MEM supplemented with 10% fetal bovine serum (fbs) and 4 ug/ml puromycin (Agapov et al., 1998). HeLa cells were maintained in DMEM supplemented with 10% fbs. All cells were incubated at 37° C. in 5% $CO_2$, unless otherwise noted.

Plasmids. SN3, a plasmid containing the RSV genome deleted for all three glycoproteins but containing the enhanced green fluorescent protein (GFP) gene was described previously (Techaarpornkul, Barretto, and Peeples, 2001)(FIG. 2). YM6 is a derivative of SN3 in which a BsiWI restriction site has been inserted immediately downstream of the L gene and the hammerhead ribozyme in SN3 has been replaced by a delta ribozyme.

Figure 3:
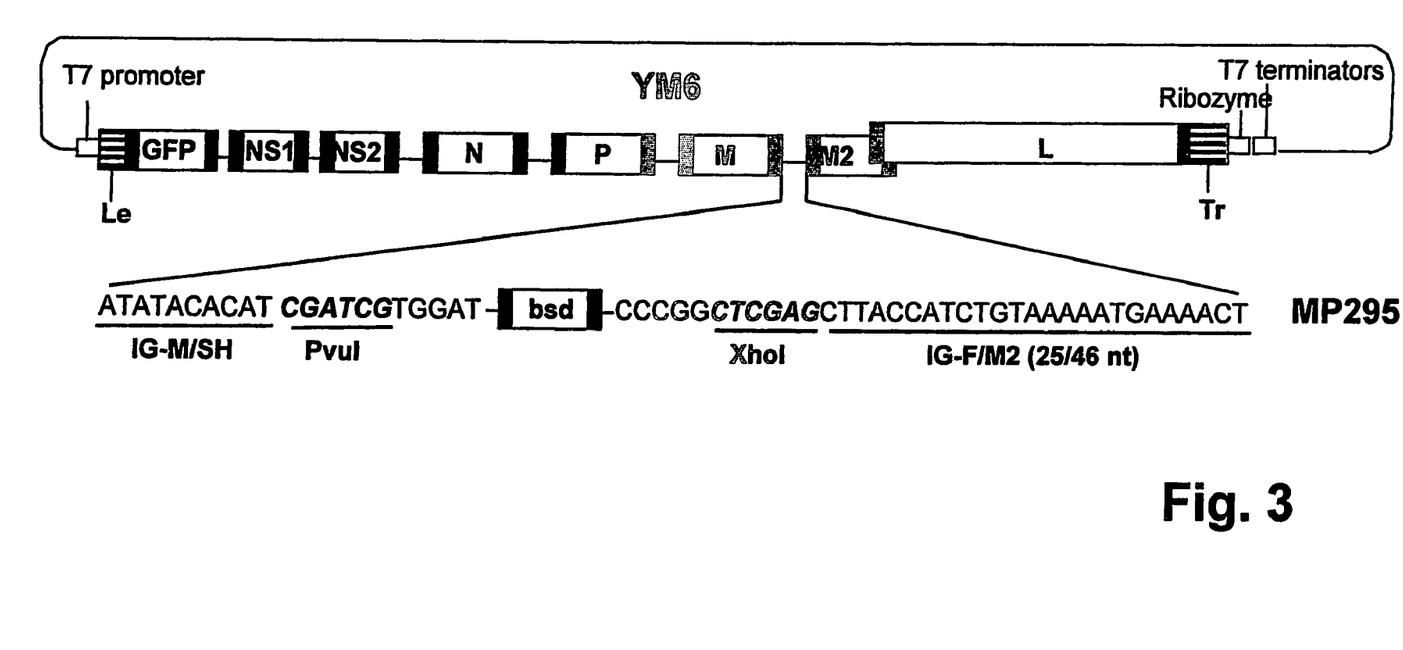
FIG. 3: Diagram of the MP295 replicon cDNA.

The blasticidin (bsd) gene was inserted into YM6 (FIG. 3). The bsd gene from pEF/Bsd (Invitrogen, Inc.) was PCR amplified using one primer containing SacII and PvuI sites and the RSV GS signal, and another primer containing the XhoI site and a consensus RSV GE sequence (TCAATAAATTTTT), in addition to sequences complementary to bsd, and inserted into the SacII and XhoI sites of pUC19 whose multiple cloning site had been modified for this purpose. The bsd gene was mutated (Byrappa, Gavin, and Gupta, 1995; Hu and Gupta, 2000) to remove an internal PvuI site and to break up a 7 base pair C+G sequence, without changing the encoded protein. This modified bsd gene unit was inserted into the PvuI and XhoI sites of YM6, yielding MP295 in which the modified bsd gene replaces the three glycoprotein genes.

The plasmid pCAGGS-G(VSV), containing the vesicular stomatitis virus G protein gene, driven by a CMV promoter, was a gift from Michael Whitt (Vanderbilt University). In all cases, plasmids were propagated in 200 ml *E. coli* DH10B cultures, and plasmid DNA was extracted and purified using Concert Maxiprep kits (Invitrogen, Inc.).

Replicon launch and selection of replicon-containing cells. The SN3 and YM6 replicons, which lack the glycoprotein genes, were launched in a manner similar to that described for recombinant infectious RSV (Collins et al., 1995), except that plasmids expressing the F and G proteins were included. HeLa cells in 35 mm tissue culture wells were transfected with SN3 or YM6 (1.2 ug), pTM1-N (0.4 ug), pTM1-P (0.2 ug), pTM1-L (0.1 ug), pTM1-M2-1 (0.1 ug), pTM1-G (0.2 ug/ml), and pTM1-F (0.2 ug/ml). TranslT-HeLa Monster (Mirus, Corp.) was used as the transfection agent. The cells were also infected with MVA-T7, a recombinant vaccinia virus that encodes T7 polymerase (Wyatt, Moss, and Rozenblatt, 1995). Cells were incubated at 33° C. The T7 polymerase transcribes each of the plasmids, enabling the initiation of RSV replication and gene expression, and the assembly of "replicon/virions." These replicon/virions were able to infect fresh HeLa cells, allowing the replicon to express its genes and to replicate, but not to produce virions.

The MP295 replicon was launched by transfecting BHK-SR19-T7 cells in 35 mm tissue culture wells with MP295 (1.2 ug), pTM1-N (0.4 ug), pTM1-P (0.2 ug), pTM1-L (0.1 ug), and pTM1-M2-1 (0.1 ug), in the absence of puromycin. TranslT-LT1 (Mirus, Corp.) was used as the transfection agent. The T7 polymerase produced by the SinRep19-T7 Sindbis virus replicon transcribed each of the plasmids, enabling the initiation of replicon gene expression and replication.

Example 1

Replication of a Glycoprotein-Deleted RSV in Cultured Cells

RSV infection of cultured cells leads to the formation of syncytia and eventually to cell death. To determine whether the glycoproteins that cause cell fusion are the only cytotoxic proteins or process of RSV replication, we used a glycoprotein-deleted RSV cDNA, SN3, that we had previously generated (Techaarpornkul, Barretto, and Peeples, 2001). This cDNA also contains a GFP gene (FIG. 1), allowing simple detection of cells in which it is replicating. A similar RSV cDNA, YM6, was also tested in this experiment.

To launch SN3 and YM6, HeLa cells in 35 mm tissue culture dishes were transfected with the SN3 plasmid and the four plasmids necessary to initiate RSV replication and transcription, N, P, L, and M2-1 (FIG. 2). Plasmids expressing the F and G glycoproteins of RSV were also transfected into these cells to enable assembly of infectious "replicon/virions" that are able to cause a single cycle of infection. The cells were infected with MVA-T7 a vaccinia virus recombinant that produces T7 polymerase. Two days after transfection green cells were visible when examined by fluorescence microscopy, indicating that both SN3 and YM6 had begun to replicate and to express their genes, including the GFP gene. Three days after transfection, virus was harvested by scraping the cells from the wells, vortexing and pelleting the cells. Fresh HeLa cells in 35 mm wells were inoculated with the supernatant.

As illustrated in FIG. 2, the seven plasmids transfected into the HeLa cells each contain a T7 promoter (black box) that is used by T7 polymerase to drive transcription. T7 polymerase is supplied by co-infection with MVA-T7. The SN3 or YM6 plasmid transcript represents the RSV genome with the additional GFP gene in the first position and all three glycoprotein genes deleted. The four support plasmids shown on the left generate mRNAs that are translated into the proteins needed to launch RSV replication. Once the replicon begins to replicate and produce its own mRNAs, the plasmids are no longer needed as a source of proteins. The two plasmids shown on the right produce the two glycoproteins that allow packaging of infectious "replicon/virions." These replicon/virions were harvested and used to infect fresh HeLa cells.

Two days after inoculation, cells were examined by fluorescence microscopy, and cell groupings counted (Table 1). Over 60% of the cells had divided once yielding pairs of cells. However, one or both of these cells had died in over 60% of these pairs. These cells were passaged to 150 mm dishes. Three days later, twice as many single green cells were observed as pairs. In addition, 3 triplet clusters and one four cell cluster were observed. Many of the single, non-dividing green cells were larger than a typical HeLa cell. An unsuccessful attempt was made to selectively isolate the multiple cell clusters. In several repeats of this rescue experiment, 8 and 16 cell clusters were observed, but selection was again unsuccessful.

These results suggested that in the absence of the glycoprotein genes, RSV is cytotoxic, though relatively slowly. Furthermore, a few cells survived infection with a replicon and some of these were able to divide several times despite the presence of the replicon.

TABLE 1

Green cells two days after transfer of replicon/virions to fresh HeLa cells

| Replicon | Singles | Pairs | Pairs with one dead cell | Pairs with both cells dead |
| --- | --- | --- | --- | --- |
| SN3 | 14 | 11 | 10 | 5 |
| SN3 | 7 | 3 | 5 | 2 |
| YM6 | 60 | 30 | 45 | 20 |
| YM6 | 40 | 27 | 20 | 9 |
| TOTAL (%) | 121 (39) | 71 (23) | 80 (26) | 36 (12) |

Example 2

Selection of Replicon-Containing Cells

Figure 1:
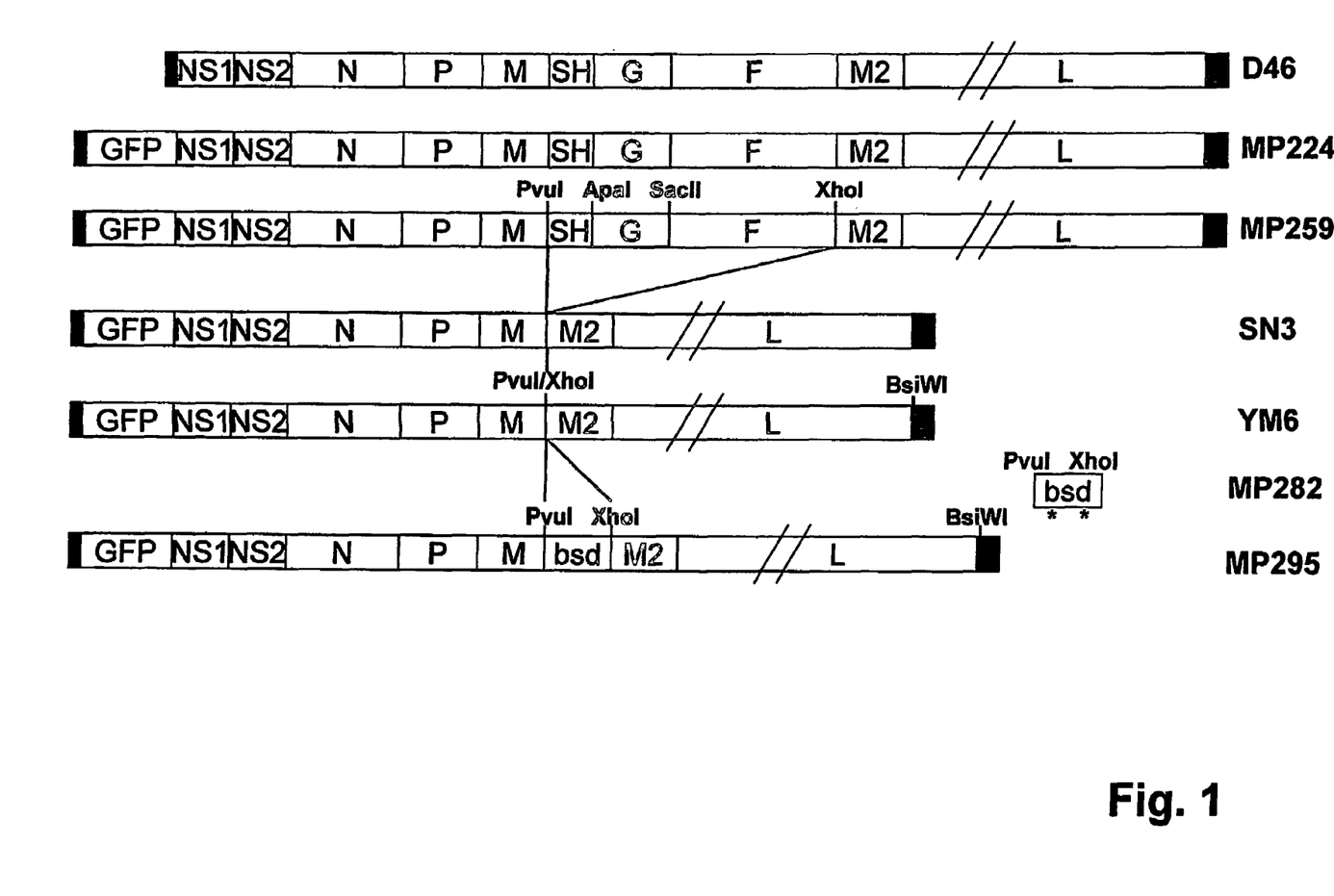
FIG. 1: Schematic diagram of cDNA clones used to generate the MP295 RSV replicon.

To allow antibiotic selection of replicon-containing cells, we inserted a blasticidin (bsd) gene unit into the former position of the viral glycoproteins to generate the RSV cDNA MP295 (FIGS. 1, 3). To simplify the launching of this replicon, we used BHK-SR19-T7 cells that produce T7 polymerase from a Sindbis virus replicon. This approach avoids vaccinia infection, and therefore, eventual death of the cells in which the replicon is functioning. It also avoids the need to produce replicon/virions for transfer of the replicons to fresh cells.

Figure 4:
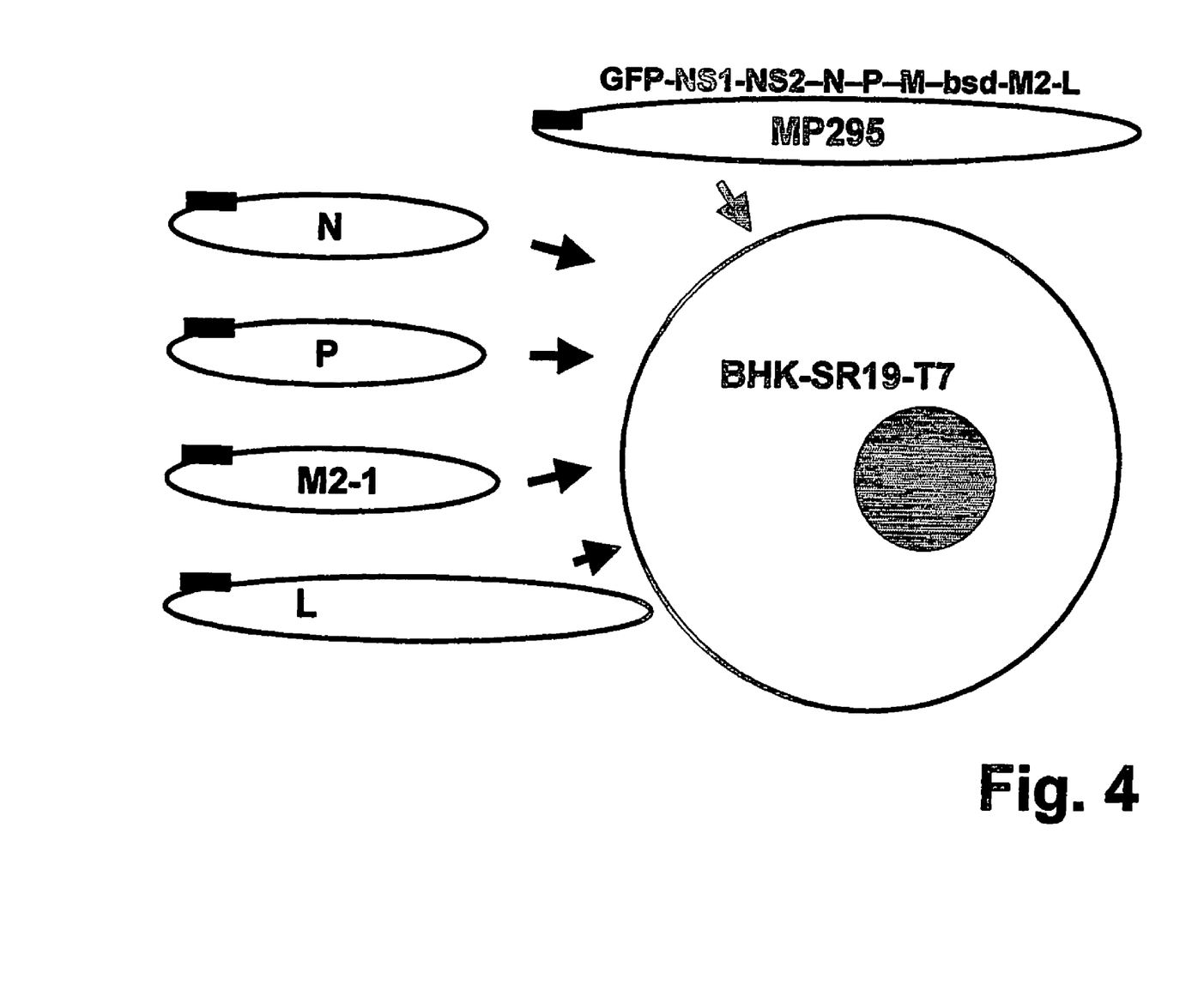
FIG. 4: Schematic representation of the lauch of replicon MP295 in BHK-SR19-T7 cells.
Figure 5:
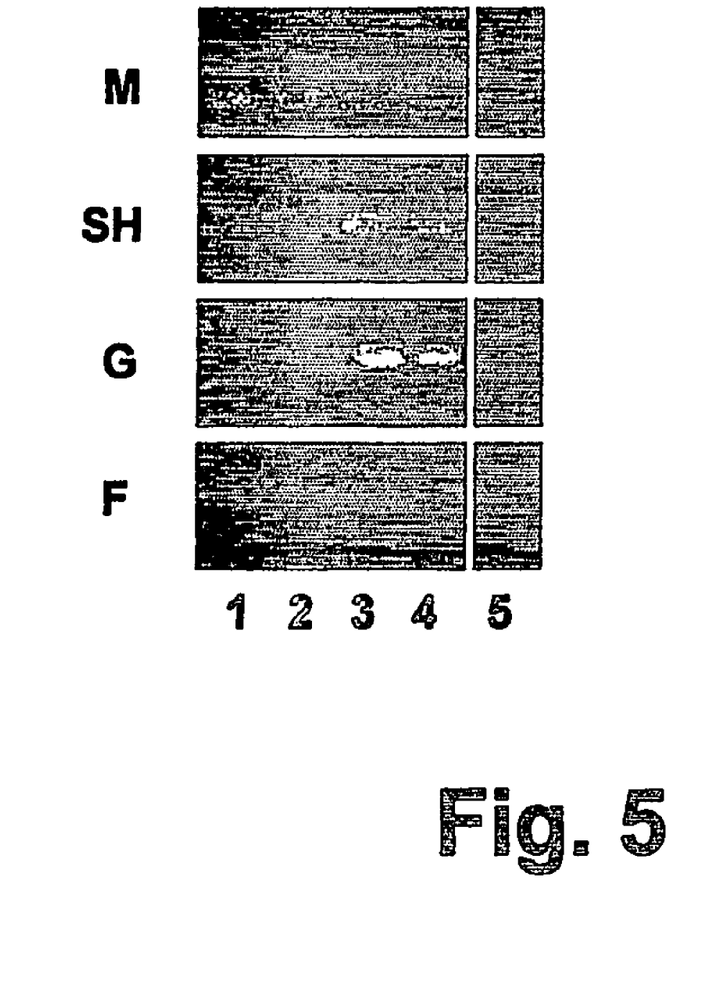
FIG. 5: RT-PCR analysis of replicon-containing cells for the presence of glycoprotein sequences.

To launch the replicon, MP295 and the four RSV support plasmids necessary for virus replication and gene expression, N, P, L, and M2-1 were transfected into two 35 mm wells of BHK-SR19-T7 cells (FIG. 4). On day 2, green cells were noted and all of the cells from each 35 mm dish were passaged to 100 mm dishes. On the following day (day 3) the medium was replaced with fresh medium containing 1 ug/ml blasticidin, a concentration that we had determined would kill most BHK-SR19-T7 cells. On day 4, approximately 200 single green cells and 15 pairs of the green cells were noted. On day 6, 20 pairs of green cells were noted. Many of the cells lacking the replicon had died by that time, but a few resistant colonies were growing. The cells were passaged into 150 mm tissue culture plates, in the presence of 4 or 8 ug/ml blasticidin in an attempt to eliminate resistant BHK cell clones. The following day, day 9, 40% of the 175 cell groups counted were pairs, the remainder being singles. By day 14, 3 colonies of >20 cells had developed, while many of the individual green cells had remained single or died. By day 19, many "mixed" colonies containing both replicon-containing and parental cells were noted, as well as more colonies with only green cells.

By day 33, many large green colonies were visible and 10 well isolated colonies were picked. Interestingly, the phenotype of these colonies fell into at least three obvious phenotypes: small (the size of the original BHK-SR19-T7 cells); large (approximately twice the size of the first phenotype); and scattered. The scattered phenotype describes cells that are localized together on the plate but rather than being in a tight cluster, they appear to be migrating away from each other. Well-isolated representatives with each of these phenotypes were cloned and grown as cell lines. Representative cell lines, BHK-RR-B51E and HeLa-RR-B51S, have been deposited with ATCC (ATCC deposit numbers: PTA-5257 and PTA-5258, respectively). Each cell line maintained its original phenotype during subsequent passages.

Cultures of BHK-RR-B51E (ATCC deposit number PTA-5257) and HeLa-RR-B51S (ATCC deposit number PTA-5258) were deposited in the permanent collection of the American Type Culture Collection (ATCC), 10801 University Blvd., Manassas, Va. 20110, U.S.A. on Jun. 12, 2003 under the terms of the Budapest Treaty, and accorded the accession numbers PTA-5257 and PTA-5258, respectively. The subject culture deposits will be stored and made available to the public in accordance with the provisions of the Budapest Treaty, i.e., they will be stored for a period of at least 30 (thirty) years after the date of deposit, or five years after the most recent request for a sample, whichever is longer. The depositor acknowledges the duty to replace the deposits with a living culture of the same should the deposited culture die or be destroyed. All restrictions on the availability to the public of the subject culture deposit will be irrevocably removed upon the granting of a patent disclosing them.

To confirm that the cells containing replicons did not contain infectious virus by accident, spent medium from the uncloned cultures was collected and used to inoculate fresh HeLa cells. No green cells were noted over the following 48 hr, though control cells inoculated with virus did produce green cells within 24 hr. In addition, we extracted RNA from the uncloned cultures, both cells and medium, and tested for the presence of SH, G, F, and M RNA. Only the M primers yielded a PCR product from the replicon-containing cells and their medium, confirming that the virus was present and replicating, but that the viral glycoprotein genes were not being expressed (FIG. 5), as expected. All four genes were detected in the cells and medium from RSV-infected cells. It is, therefore, possible to biologically select cells containing stable, replicating, non-cytotoxic RSV replicons.

Example 3

Replicon Mobilization

To determine whether the cells or the replicons had been selected, the replicons from three of the replicon-containing cell lines, one from each cell phenotype, were transferred to fresh cells. To accomplish this transfer, the replicons were "mobilized" by supplying a viral glycoprotein gene that allows virion formation, the VSV G gene (FIG. 6). Three days post-transfection the "replicon/virions" in the medium were used to inoculate fresh BHK-SR19-T7 cells, as well as HeLa cells.

The day after inoculation, many cells in each of the inoculated dishes were green. In one dish, more than 1,000 of the cells were green. On day 3, all of the cells were passaged from 35 mm dishes to 100 mm dishes, and 8 ug/ml blasticidin was added the following day with fresh medium. Cells lacking replicons died over the following week. Most of the green cells developed into clones. The large die-off noted during their initial isolation did not occur, indicating that non-cytotoxic replicons had been selected in the initial BHK-SR19-T7 cells, not cells that could cope with the infection. Both BHK-SR19-T7 and HeLa cells displayed this non-cytotoxic, rapid colony development pattern, indicating that these replicons that had been selected for non-cytotoxicity in one cell line are also non-cytotoxic in another, even a cell line from another species.

Interestingly, the small, large and scattered cell phenotypes noted in the original replicon-containing BHK-SR19-T7 cell clones were also found in the BHK-SR19-T7 cells that received the mobilized replicon. But instead of finding the same phenotype as the original replicon-containing cells, all three phenotypes were found in the clones initiated from each replicon/virion preparation. This result indicates that the replicons were not the cause the different cell phenotypes. Perhaps the BHK-SR19-T7 cells contain a mixture of cell phenotypes which can support a non-cytopathic RSV replicon. Several similar cell phenotypes were also observed in the HeLa cells inoculated with replicon/virions from each original BHK clone.

REFERENCES

Agapov, E. V., Frolov, I., Lindenbach, B. D., Pragai, B. M., Schlesinger, S., and Rice, C. M. (1998). Noncytopathic Sindbis virus RNA vectors for heterologous gene expression [see comments]. *Proc Natl Acad Sci U S A* 95(22), 12989-94.

Bermingham, A., and Collins, P. L. (1999). The M2-2 protein of human respiratory syncytial virus is a regulatory factor involved in the balance between RNA replication and transcription. *Proc Natl Acad Sci U S A* 96(20), 11259-64.

Blight, K. J., Kolykhalov, A. A., and Rice, C. M. (2000). Efficient initiation of HCV RNA replication in cell culture. *Science* 290(5498), 1972-4.

Byrappa, S., Gavin, D. K., and Gupta, K. C. (1995). A highly efficient procedure for site-specific mutagenesis of full-length plasmids using Vent DNA polymerase. *Genome Res* 5(4), 404-7.

Cathomen, T., Naim, H. Y., and Cattaneo, R. (1998). Measles viruses with altered envelope protein cytoplasmic tails gain cell fusion competence. *J Virol* 72(2), 1224-34.

Collins, P. L., Hill, M. G., Camargo, E., Grosfeld, H., Chanock, R. M., and Murphy, B. R. (1995). Production of infectious human respiratory syncytial virus from cloned cDNA confirms an essential role for the transcription elongation factor from the 5' proximal open reading frame of the M2 mRNA in gene expression and provides a capability for vaccine development. *Proc Natl Acad Sci U S A* 92(25), 11563-7.

Collins, P. L., Hill, M. G., Cristina, J., and Grosfeld, H. (1996). Transcription elongation factor of respiratory syncytial virus, a nonsegmented negative-strand RNA virus. *Proc Natl Acad Sci U S A* 93(1), 81-5.

Collins, P. L., McIntosh, K., and Chanock, R. M. (2001). Respiratory syncytial virus. 4th ed. In "Fields Virology" (D. M. Knipe, and P. M. Howley, Eds.), Vol. 1, pp. 1443-1486. Lippincott-Raven, Philadelphia.

Falsey, A. R., and Walsh, E. E. (2000). Respiratory syncytial virus infection in adults. *Clin Microbiol Rev* 13(3), 371-84.

Frolov, I., Agapov, E., Hoffman, T. A., Jr., Pragai, B. M., Lippa, M., Schlesinger, S., and Rice, C. M. (1999). Selection of RNA replicons capable of persistent noncytopathic replication in mammalian cells. *J Virol* 73(5), 3854-65.

Hallak, L., Spillman, D, Collins, P L, and Peeples, M E (2000). Glycosaminoglycan sulfation requirements for respiratory syncytial virus infection. *J. Virol.* 74, 10508-10513.

Heilman, C. A. (1990). From the National Institute of Allergy and Infectious Diseases and the World Health Organization. Respiratory syncytial and parainfluenza viruses. *J Infect Dis* 161(3), 402-6.

Hu, C., and Gupta, K. C. (2000). Functional significance of alternate phosphorylation in Sendai virus P protein. *Virology* 268(2), 517-32.

Inoue, M., Tokusumi, Y., Ban, H., Kanaya, T., Shirakura, M., Tokusumi, T., Hirata, T., Nagai, Y., Iida, A., and Hasegawa, M. (2003). A New Sendai Virus Vector Deficient in the Matrix Gene Does Not Form Virus Particles and Shows Extensive Cell-to-Cell Spreading. *J Virol* 77(11), 6419-29.

Karron, R. A., Buonagurio, D. A., Georgiu, A. F., Whitehead, S. S., Adamus, J. E., Clements-Mann, M. L., Harris, D. O., Randolph, V. B., Udem, S. A., Murphy, B. R., and Sidhu, M. S. (1997). Respiratory syncytial virus (RSV) SH and G proteins are not essential for viral replication in vitro: clinical evaluation and molecular characterization of a cold-passaged, attenuated RSV subgroup B mutant. *Proc Natl Acad Sci U S A* 94(25), 13961-6.

Levine, S., Peeples, M., and Hamilton, R. (1977). Effect of respiratory syncytial virus infection of HeLa-cell macromolecular synthesis. *J Gen Virol* 37(1), 53-63.

Li, H. O., Zhu, Y. F., Asakawa, M., Kuma, H., Hirata, T., Ueda, Y., Lee, Y. S., Fukumura, M., Iida, A., Kato, A., Nagai, Y., and Hasegawa, M. (2000). A cytoplasmic RNA vector derived from nontransmissible Sendai virus with efficient gene transfer and expression. *J Virol* 74(14), 6564-9.

Lohmann, V., Korner, F., Koch, O., Herian, U., Theilmann, L., and Bartenschlager, R. (1999). Replication of subgenomic hepatitis C virus RNAs in a hepatoma cell line. *Science* 285, 110-113.

Russell, C. J., Jardetzky, T. S., and Lamb, R. A. (2001). Membrane fusion machines of paramyxoviruses: capture of intermediates of fusion. *Embo J* 20(15), 4024-34.

Schmitt, A. P:, Leser, G. P., Waning, D. L., and Lamb, R. A. (2002). Requirements for budding of paramyxovirus simian virus 5 virus-like particles. *J Virol* 76(8), 3952-64.

Techaarpornkul, S., Barretto, N., and Peeples, M. E. (2001). Functional analysis of recombinant respiratory syncytial virus deletion mutants lacking the small hydrophobic and/or attachment glycoprotein gene. *J Virol* 75(15), 6825-34.

Waning, D. L., Schmitt, A. P., Leser, G. P., and Lamb, R. A. (2002). Roles for the cytoplasmic tails of the fusion and hemagglutinin-neuraminidase proteins in budding of the paramyxovirus simian virus 5. *J Virol* 76(18), 9284-97.

Wyatt, L. S., Moss, B., and Rozenblatt, S. (1995). Replication-deficient vaccinia virus encoding bacteriophage T7 RNA polymerase for transient gene expression in mammalian cells. *Virology* 210(1), 202-5.

Zhang, L., Peeples, M. E., Boucher, R. C., Collins, P. L., and Pickles, R. J. (2002). Respiratory syncytial virus infection of human airway epithelial cells is polarized, specific to ciliated cells, and without obvious cytopathology. *J Virol* 76(11), 5654-66.

Zimmer, G., Budz, L., and Herrier, G. (2001). Proteolytic activation of respiratory syncytial virus fusion protein. Cleavage at two furin consensus sequences. *J Biol Chem* 276(34), 31642-50.

b) a nucleotide sequence encoding a selectable marker suitable for selection, wherein said sequence encoding a selectable marker is under the control of the respiratory syncytial virus replication machinery, wherein the replicon can be used to biologically select cells containing stable, replicating, replicons, and wherein said replicon is non-cytotoxic to said cells when said cells do not express F, G, and SH viral glycoproteins.

2. The replicon of claim 1, wherein said sequence encoding a selectable marker is a gene that confers resistance to an antibiotic.

3. The replicon of claim 2 wherein said gene is a bsd gene.

4. The replicon of claim 1, further comprising a sequence encoding a heterologous protein.

5. The replicon of claim 1 further comprising a reporter gene.

6. The replicon of claim 5, wherein said reporter gene is a gene encoding green fluorescent protein (GFP).

7. The replicon of claim 1, wherein the sequence encoding the F, G and SH glycoproteins is deleted.

8. The replicon of claim 7 wherein said sequence encoding a selectable marker is a gene that confers resistance to an antibiotic.

9. The replicon of claim 8, wherein said gene is a bsd gene.

10. The replicon of claim 9, further comprising a reporter gene.

11. The replicon of claim 10 wherein said reporter gene is a gene encoding GFP.

12. A cell line comprising the replicon of claim 1.

13. The replicon of claim 11, wherein said replicon is harbored in a cell line selected from the group consisting of BHK-RR-B51E (ATCC deposit number PTA-5257) and HeLa-RR-B51S (ATCC deposit number PTA-5258).

14. The replicon of claim 11, further comprising a sequence encoding a heterologous protein.

15. A plasmid encoding a cDNA of a negative-strand respiratory syncytial virus (RSV) replicon comprising

What is claimed is:

1. A synthetic negative-strand respiratory syncytial virus (RSV) replicon comprising a) a nucleotide sequence of said respiratory syncytial virus, wherein the sequences encoding the F, G and SH glycoproteins are inactivated or deleted; and a) a nucleotide sequence complementary to the genome of a non-cytopathic negative-strand respiratory syncytial virus (RSV), wherein the sequences encoding F, G, and SH glycoprotein gene units are inactivated or deleted;
b) a nucleotide sequence comprising a heterologous promoter sequence operatively linked to said sequence of a); and
c) a nucleotide sequence comprising a gene encoding a selectable marker suitable for selection, wherein said gene is under the control of the RNA virus replication machinery, wherein the replicon can be used to biologically select cells containing stable, replicating, replicons, and wherein said replicon is non-cytotoxic to said cells when said cells do not express F, G, and SH viral glycoproteins.

16. The plasmid of claim 15, wherein said heterologous promoter sequence is selected from the group consisting of T7 polymerase promoter, cytomegalovirus immediate early promoter, SV40 early promoter and polymerase I promoter.

17. The plasmid of claim 15 wherein said promoter is a T7 polymerase promoter.

18. A replicon encoded by the plasmid of claim 15.

* * * * *

UNITED STATES PATENT AND TRADEMARK OFFICE
CERTIFICATE OF CORRECTION

PATENT NO. : 7,585,667 B2 Page 1 of 1
APPLICATION NO. : 10/560655
DATED : September 8, 2009
INVENTOR(S) : Paul D. Olivo, Peter L. Collins and Mark E. Peeples It is certified that error appears in the above-identified patent and that said Letters Patent is hereby corrected as shown below:

On Page 1, in Field (73) Assignees should read: --Apath, LLC, St. Louis, MO (US);-- The United States of America as represented by The Department of Health and Human Services, Washington, DC (US); Rush University Medical Center, Chicago, IL (US)

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,585,667 B2 | Page 1 of 1 |
| APPLICATION NO. | : 10/560655 | |
| DATED | : September 8, 2009 | |
| INVENTOR(S) | : Olivo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 294 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
atatacacat cgatcgtgga t                                      21

<210> SEQ ID NO 2
<211> LENGTH: 36
<212> TYPE: DNA
<213> ORGANISM: Artificial Sequence
<220> FEATURE:
<223> OTHER INFORMATION: Synthetic

<400> SEQUENCE: 2
cccggctcga gcttaccatc tgtaaaaatg aaaact                      36
```